(12) United States Patent
Kuboi et al.

(10) Patent No.: US 12,075,982 B2
(45) Date of Patent: Sep. 3, 2024

(54) LIGHT SOURCE DEVICE HAVING ILLUMINATION CONTROLLER CONTROLLING MULTIPLE LIGHT SOURCES IN MULTIPLE STATES, CONTROL METHOD OF THE LIGHT SOURCE, AND ENDOSCOPE SYSTEM HAVING THE LIGHT SOURCE

(71) Applicant: OLYMPUS CORPORATION, Tokyo (JP)

(72) Inventors: Toru Kuboi, Machida (JP); Hiroaki Kitamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 847 days.

(21) Appl. No.: 17/119,380

(22) Filed: Dec. 11, 2020

(65) Prior Publication Data

US 2021/0127946 A1    May 6, 2021

Related U.S. Application Data

(63) Continuation of application No. PCT/JP2019/006610, filed on Feb. 21, 2019.

(30) Foreign Application Priority Data

Jun. 25, 2018  (JP) .................... 2018-119759

(51) Int. Cl.
*A61B 1/06*    (2006.01)
*A61B 1/00*    (2006.01)

(52) U.S. Cl.
CPC ........ *A61B 1/0638* (2013.01); *A61B 1/00006* (2013.01); *A61B 1/063* (2013.01); *A61B 1/0655* (2022.02); *A61B 1/00009* (2013.01)

(58) Field of Classification Search
None
See application file for complete search history.

(56) References Cited

U.S. PATENT DOCUMENTS

2003/0035048 A1* 2/2003 Shipp ............... A61B 1/0684
                                                348/E7.087
2003/0174208 A1* 9/2003 Glukhovsky ...... G02B 23/2461
                                                348/E5.029

(Continued)

FOREIGN PATENT DOCUMENTS

JP    2009-178180 A    8/2009
JP    2011-224043 A    11/2011

(Continued)

OTHER PUBLICATIONS

Japanese Office Action dated Jul. 19, 2022 received in 2020-527190.

(Continued)

*Primary Examiner* — John P Leubecker
(74) *Attorney, Agent, or Firm* — Scully, Scott, Murphy & Presser, P.C.

(57) ABSTRACT

A light source device includes: a first light emitter configured to emit first light; a second light emitter configured to emit second light having an identical color component to the first light; and an illumination controller configured to cause, after causing the first light emitter to emit the first light, the second light emitter to emit the second light according to a set light amount in a state in which the first light emitter is caused to emit the first light.

19 Claims, 10 Drawing Sheets

(56) References Cited

U.S. PATENT DOCUMENTS

| | | | |
|---|---|---|---|
| 2008/0297059 A1* | 12/2008 | Nisani | H05B 45/46 |
| | | | 315/185 R |
| 2011/0257483 A1* | 10/2011 | Mizuyoshi | G02B 23/2469 |
| | | | 362/555 |
| 2011/0257484 A1 | 10/2011 | Mizuyoshi et al. | |
| 2012/0319616 A1* | 12/2012 | Quilici | F21V 5/007 |
| | | | 362/244 |
| 2013/0093362 A1* | 4/2013 | Edwards | F21S 4/28 |
| | | | 359/326 |
| 2013/0193875 A1* | 8/2013 | Godo | A61B 1/044 |
| | | | 315/297 |
| 2015/0009677 A1* | 1/2015 | Catalano | F21S 10/00 |
| | | | 362/296.07 |
| 2015/0185414 A1 | 7/2015 | Baumann | |
| 2016/0249793 A1* | 9/2016 | Wang | A61B 5/073 |
| | | | 600/109 |
| 2016/0302275 A1* | 10/2016 | Newton | H05B 45/10 |
| 2018/0090290 A1* | 3/2018 | Morgenshtein | G01J 1/44 |

FOREIGN PATENT DOCUMENTS

| | | |
|---|---|---|
| JP | 2012-245349 A | 12/2012 |
| WO | 2012/105446 A1 | 8/2012 |

OTHER PUBLICATIONS

International Search Report dated Apr. 16, 2019 received in PCT/JP2019/006610.

\* cited by examiner

FIG.5A
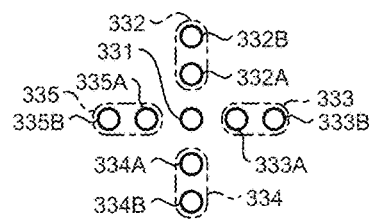
FIG.5B
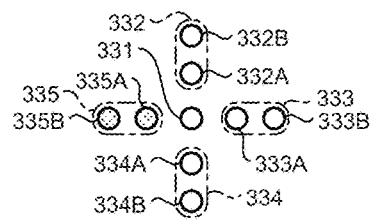
FIG.5C
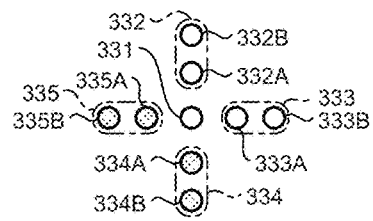
FIG.5D
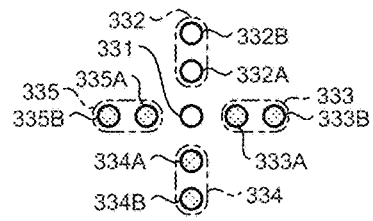
FIG.5E
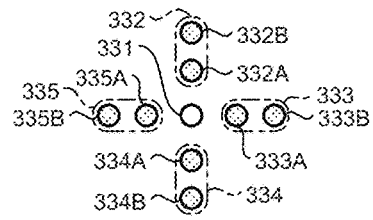
FIG.5F
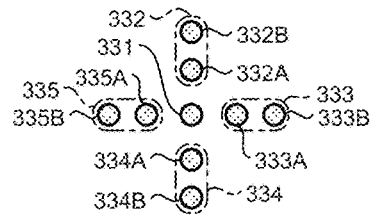

FIG.7A
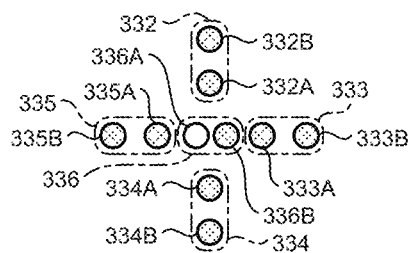
FIG.7B
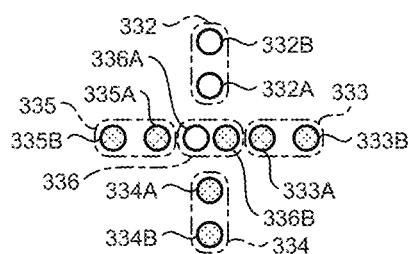
FIG.7C
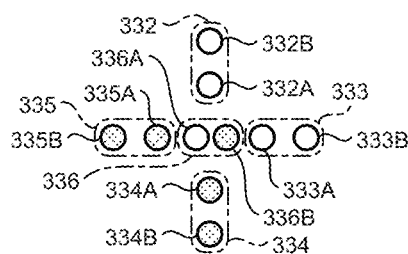
FIG.7D
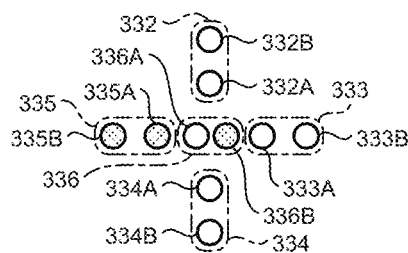
FIG.7E
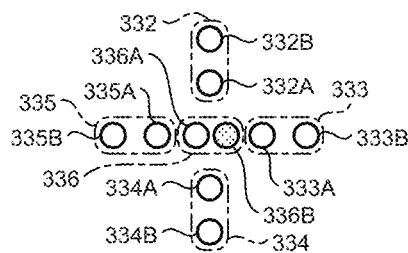

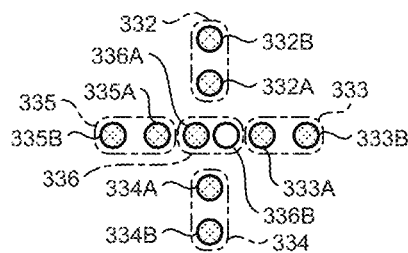
FIG.9A
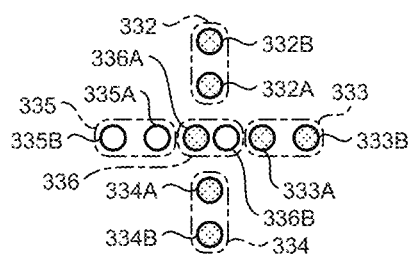
FIG.9B
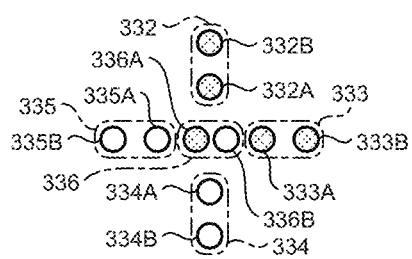
FIG.9C
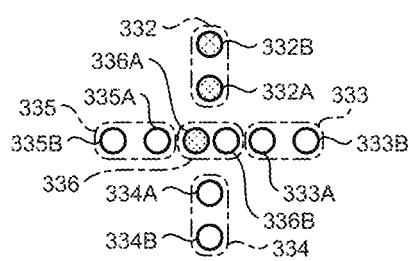
FIG.9D
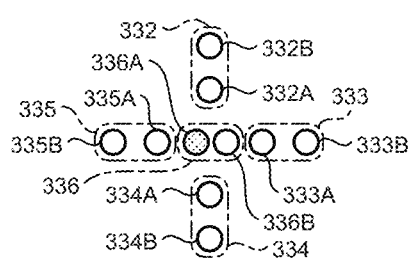
FIG.9E FIG.10A
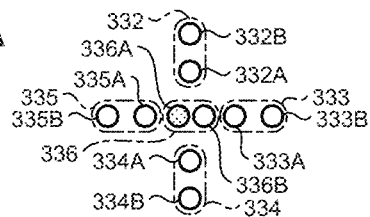
FIG.10B
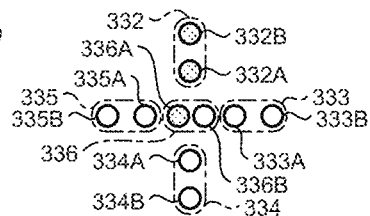
FIG.10C
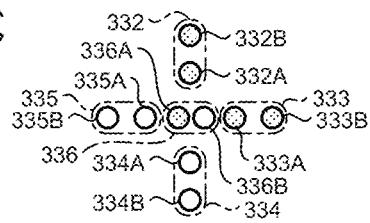
FIG.10D
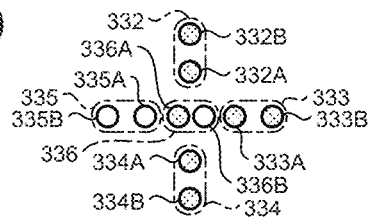
FIG.10E
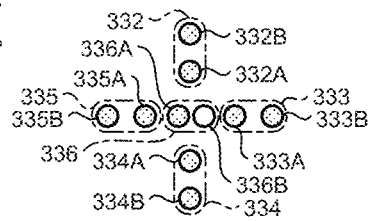
FIG.10F
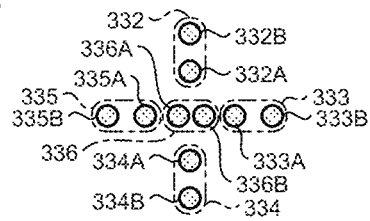

LIGHT SOURCE DEVICE HAVING ILLUMINATION CONTROLLER CONTROLLING MULTIPLE LIGHT SOURCES IN MULTIPLE STATES, CONTROL METHOD OF THE LIGHT SOURCE, AND ENDOSCOPE SYSTEM HAVING THE LIGHT SOURCE

CROSS-REFERENCE TO RELATED APPLICATIONS

This application is a continuation of PCT international application No. PCT/JP2019/006610 filed on Feb. 21, 2019, which designates the United States, incorporated herein by reference, and which claims the benefit of priority from Japanese Patent Application No. 2018-119759, filed on Jun. 25, 2018, incorporated herein by reference.

BACKGROUND

1. Technical Field

The present disclosure relates to a light source device, a control method of a light source, and an endoscope system.

2. Related Art

In the field of medicine, endoscope systems are used to observe the inside of a subject. Generally, an endoscope captures an in-vivo image by inserting a long and thin flexible insertion portion into the body of a subject, such as a patient, by illuminating with illumination light supplied by a light source device from a distal end of this insertion portion, and by receiving reflected light of this illumination light with an imaging unit at the distal end of the insertion portion. The in-vivo image captured by the imaging unit of the endoscope is subjected to predetermined image processing by a processing device of the endoscope system, and then displayed on a display of the endoscope system. A user, such as a medical doctor, observes an organ of the subject based on the in-vivo image displayed on the display.

As for the light source device that emits illumination light, for example, a light source device in which plural light sources emitting the same light are provided to expand a dynamic range of a light amount control has been disclosed, for example, in JP-A-2012-245349. Moreover, in the technique disclosed in JP-A-2012-245349, light emitting order of the light sources is determined based on cumulative light emitting time of the respective light sources.

SUMMARY

In some embodiments, a light source device includes: a first light emitter configured to emit first light; a second light emitter configured to emit second light having an identical color component to the first light; and an illumination controller configured to cause, after causing the first light emitter to emit the first light, the second light emitter to emit the second light according to a set light amount in a state in which the first light emitter is caused to emit the first light.

In some embodiments, provided is a control method of a light source including a first light emitter configured to emit first light; a second light emitter configured to emit second light having an identical component to the first light. The method includes: causing the first light emitter to emit the first light; and causing the second light emitter to emit the second light according to a set light amount in a state in which the first light emitter is caused to emit the first light.

In some embodiments, an endoscope system includes: an endoscope; and a light source device that includes a first light emitter configured to emit first light to be supplied to the endoscope; a second light emitter configured emit second light having an identical color component to the first light; and an illumination controller configured to cause, after causing the first light emitter to emit the first light, the second light emitter to emit the second light according to a set light amount in a state in which the first light emitter is caused to emit the first light.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIGS. 5A-5F are diagrams for explaining light-off order of the light sources of the light source device included in the endoscope system according to the first embodiment;

FIGS. 7A-7E are diagrams for explaining light-on order of the light sources in a first light-on mode of the light source device included in the endoscope system according to the second embodiment;

FIGS. 9A-9E are diagrams for explaining light-on order of the light sources in a second light-on mode of the light source device included in the endoscope system according to the second embodiment; and FIGS. 10A-10F are diagrams for explaining light-off order of the light sources in the second light-on mode of the light source device included in the endoscope system according to the second embodiment.

DETAILED DESCRIPTION

Hereinafter, modes (hereinafter, "embodiments") to implement the present disclosure will be explained. In the embodiments, a medical endoscope system that captures and displays an image of an inside of a subject, such as a patient will be explained as an example of a system including a light source device according to the present disclosure. The embodiments are not intended to limit the present disclosure. Furthermore, explanation will be given, assigning identical reference symbols to identical parts throughout the drawings.

Figure 1:
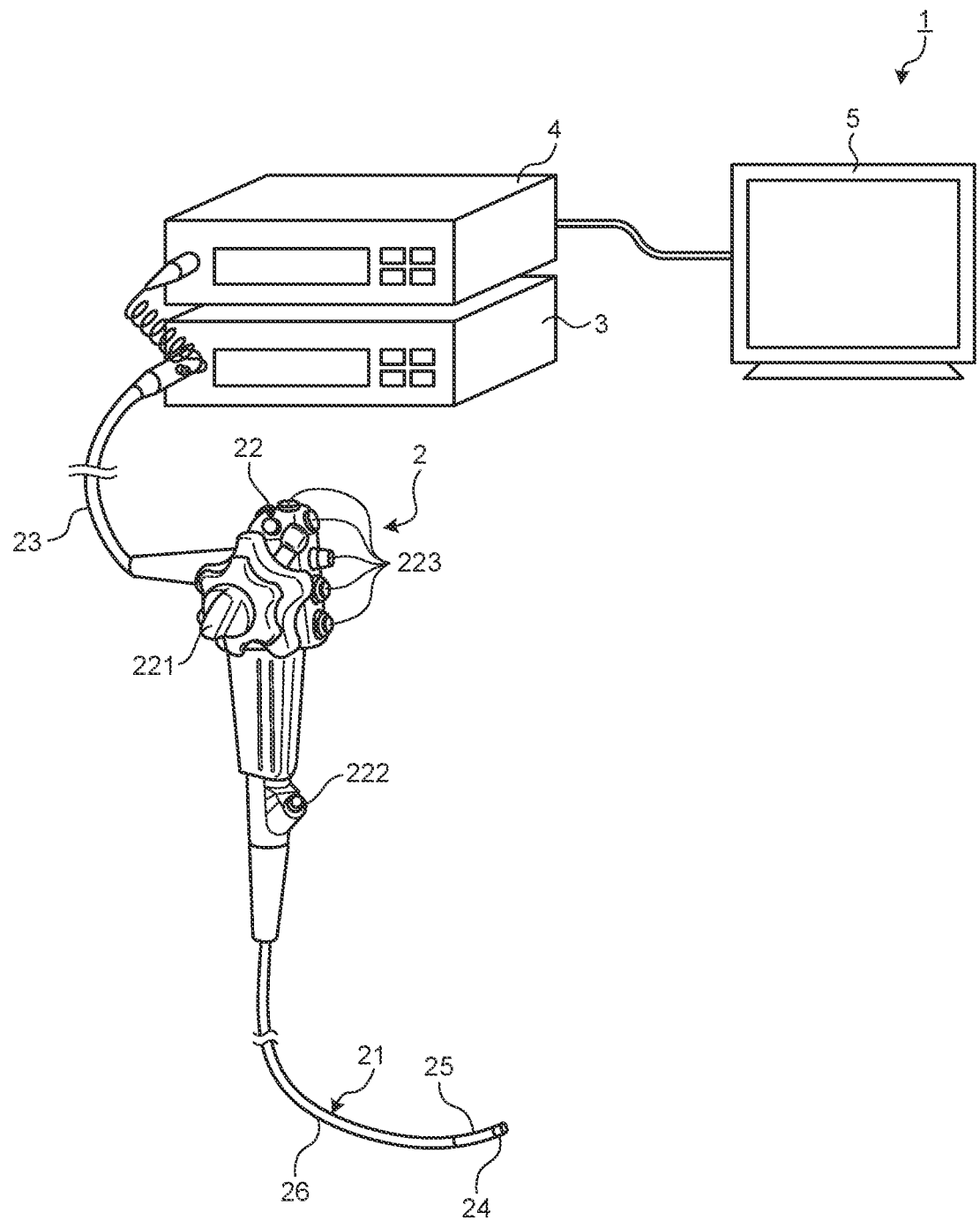
FIG. 1 is a diagram illustrating a schematic configuration of an endoscope system according to a first embodiment.
Figure 2:
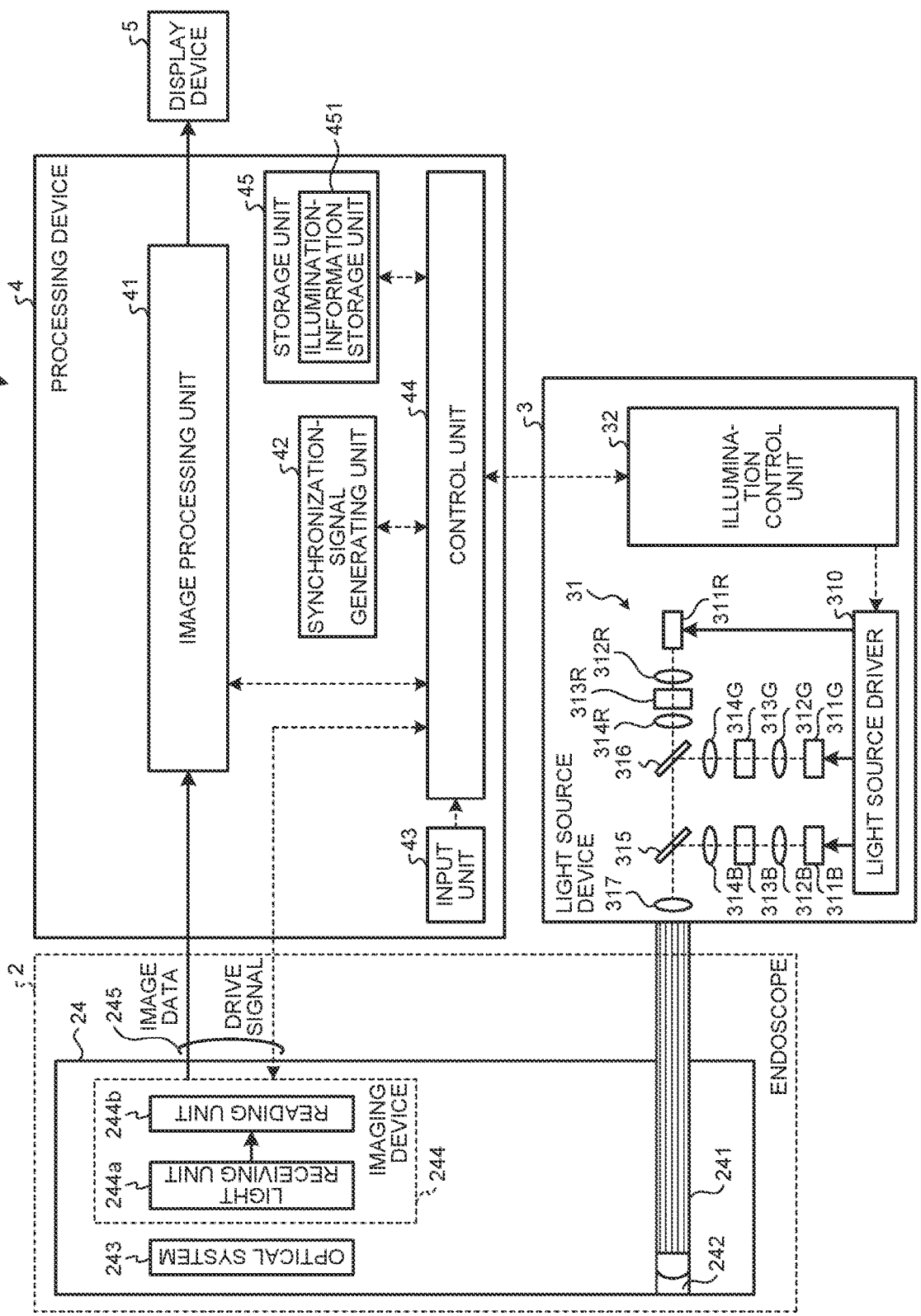
FIG. 2 is a block diagram illustrating a schematic configuration of the endoscope system according to the first embodiment.

FIG. 1 is a diagram illustrating a schematic configuration of an endoscope system according to a first embodiment. FIG. 2 is a block diagram illustrating a schematic configuration of the endoscope system according to the first embodiment.

An endoscope system 1 illustrated in FIG. 1 and FIG. 2 includes an endoscope 2 that captures an in-vivo image of a subject by inserting a distal end portion into a body of the subject, a light source device 3 that generates illumination light emitted from a distal end of the endoscope 2, a processing device 4 that subjects an image signal captured by the endoscope 2 to predetermined signal processing, and that performs an overall control of the operation of the entire endoscope system 1, and a display device 5 that displays the in-vivo image generated by the signal processing of the processing device 4.

The endoscope 2 includes a flexible long and thin insertion portion 21, an operating unit 22 that is connected to a proximal end portion of the insertion portion 21 and that receives an input of various kinds of operation signals, and a universal cord 23 that extends in a direction different from a direction in which the insertion portion 21 extends from the operating unit 22, and that has various kinds of cables connecting the light source device 3 and the processing device 4 inside.

The insertion portion 21 includes a distal end portion 24 that is equipped with two-dimensionally aligned imaging devices 244 that receive light and perform photoelectric conversion, to generate a signal, a bendable portion 25 that is constituted of plural bending pieces to be bendable, and a flexible tube 26 that is flexible and long-shaped, and that is connected to a proximal end portion of the bendable portion 25. The insertion portion 21 is inserted into a body cavity of the subject, and images a subject, such as a living tissue, at a position at which outside light cannot reach by the imaging device 244.

The distal end portion 24 includes a light guide 241 that is formed using a glass fiber or the like, and that forms a light guiding path for light emitted by the light source device 3, an illumination lens 242 that is arranged at a distal end of the light guide 241, an optical system 243 for light condensing, and the imaging device 244 (imaging unit) that is arranged at an image forming position of the optical system 243, and that receives light condensed by the optical system 243 to convert into an electrical signal by performing photoelectric conversion, and that subjects it to predetermined signal processing.

The optical system 243 is constituted of one or more lenses, and has an optical zoom function that changes an angle of view, and a focus function that changes a focal point.

The imaging device 244 generates an electrical signal (image signal) by photoelectric-converting light from the optical system 243. Specifically, the imaging device 244 includes a light receiving unit 244a in which plural pixels each including a photodiode that accumulates an electric charge according to a light amount, a capacitor that converts an electric charge transferred from the photodiode into a voltage level, or the like are arranged in a matrix shape, and in which each pixel generates an electrical signal by photoelectric converting light from the optical system 243, and a reading unit 244b that sequentially reads electrical signals generated by pixels that are arbitrarily configured to be read out of the plural pixels of the light receiving unit 244a, to output as image signals. The imaging device 244 is implemented by using, for example, a charge coupled device (CCD) image sensor, or a complementary metal oxide semiconductor (CMOS) image sensor.

The endoscope 2 has a memory (not shown) that stores an execution program and a control program for the imaging device 244 to perform various kinds of operations, and data including identification information of the endoscope 2. The identification information includes inherent information (ID) of the endoscope 2, a model year, specification information, a transmission mode, and the like. Moreover, the memory may temporarily store image data generated by the imaging device 244 and the like.

The operating unit 22 includes a bending knob 221 that bends the bendable portion 25 in an up-and-down direction and a left-and-right direction, a treatment-tool inserting portion 222 to insert a treatment tool, such as biopsy forceps, an electrosurgical knife, and an inspection probe, into a body cavity of the subject, and plural switches 223 serving as an operation input unit that inputs an operation instruction signal for a peripheral devices, such as an air feeding means, a water feeding means, and a screen display control, in addition to the processing device 4. The treatment tool inserted from the processing-tool inserting portion 222 is exposed out from an opening portion (not shown) through a treatment tool channel (not shown) of the distal end portion 24.

The universal cord 23 has therein at least the light guide 241 and a bundled cable 245 in which one or more cables are bundled. The bundled cable 245 includes a signal wire to transmit an image signal, a signal wire to transmit a drive signal to drive the imaging device 244, and a signal wire to communicate information including inherent information about the endoscope 2 (the imaging devices 244), and the like. In the present embodiment, it will be explained such that an electrical signal is transmitted using the signal wire, but it may be used to transmit an optical signal, or may be used to transmit a signal between the endoscope 2 and the processing device 4 by wireless communication.

Subsequently, a configuration of the light source device 3 will be explained. The light source device 3 includes a light source unit 31 and an illumination control unit 32.

The light source unit 31 is constituted of plural light sources that emit plural illumination lights having wavelength bands different from one another, plural lenses, and the like, and emits illumination light including light of a predetermined wavelength by driving of each light source. Specifically, the light source unit 31 includes a light source driver 310, a first light-source group 311B that emits light (blue illumination light) having a wavelength band of 390 nm to 495 nm, a second light-source group 311G that emits light (green illumination light) having a wavelength band of 495 nm to 590 nm, a third light-source group 311R (red illumination light) having a wavelength band of 590 nm to 750 nm, first lenses (first lenses 312B, 312G, 312R) that respectively gather illumination lights emitted by the respective light sources, light amount sensors (light amount sensors 313B, 313G, 313R) that respectively detect a light amount of illumination light that has passed through the first lens, second lenses (second lenses 314B, 314G, 314R) that respectively gather illumination lights that have passed through the light amount sensors, a dichroic mirror 315 that bends light of a wavelength band emitted by the first light source group 311B, and lets light of other wavelength bands pass through, a dichroic mirror 316 that bends light of a wavelength band emitted by the second light source group 311G, and lets light of other wavelengths bands pass through, and a lens 317 that guides light of wavelengths emitted by the respective light sources to the light guide 241.

The respective light source groups are implemented by using plural semiconductor lasers, plural LED light sources, or the like. The dichroic mirrors 315, 316 bend light from the light source groups to make them travel along the same optical axis.

Each of the light amount sensor has a diffuser arranged therein, and emits incident illumination light in a diffused manner. The light amount sensor acquires a part of light emitted by a light source before (or after) passing through the diffuser, and outputs its light amount value, or outputs an estimated value of a light amount of light that has been emitted by the light source based on the light amount value of the acquired light.

In the light sources, a cooling mechanism to cool down a heat generated at the time of driving is provided. The cooling mechanism is constituted of a Peltier device, heat sink, or the like.

The light source driver 310 causes the light sources to emit light by supplying an electric current to the respective light source groups under control of the illumination control unit 32.

In the light source unit 31, the first light source group 311B, the second light source group 311G, and the third light source group 311R are controlled to emit illumination light in respective different timing, to emit illumination light of a single color to the outside, or controlled to emit light from all of the light sources, to emit illumination light of white color to the outside.

The illumination control unit 32 controls a power amount to be supplied to the respective light sources based on a control signal (light modulation signal) from the control unit 44, and controls driving timing of the respective light sources.

Next, a configuration of the processing device 4 will be explained. The processing device 4 includes an image processing unit 41, a synchronization-signal generating unit 42, an input unit 43, a control unit 44, and a storage unit 45.

The image processing unit 41 receives image data of illumination light of respective colors captured by the imaging device 244 from the endoscope 2. When analog image data is received from the endoscope 2, the image processing unit 41 performs A/D conversion, to generate a digital image signal. Moreover, when image data is received as an optical signal from the endoscope 2, the image processing unit 41 performs photoelectric conversion, to generate digital image data.

The image processing unit 41 subjects image data received from the endoscope 2 to predetermined image processing to generate an image, and outputs it to the display device 5. The predetermined processing includes synchronization processing, tone correction processing, color correction processing, and the like. The synchronization processing is processing of synchronizing respective pieces of R image data based on image data generated by the imaging device 244 at the time of irradiation of R illumination light by the light source unit 31, G image data based on image data generated by the imaging device 244 at the time of irradiation of G illumination light by the light source unit 31, and B image data based on image data generated by the imaging device 244 at the time of irradiation of B illumination by the light source unit 31. The tone correction processing is processing of performing correction of tones with respect to the image data. The color correction processing is processing of performing color correction with respect to the image data. The image processing unit 41 generates a processed image signal including an in-vivo image that has been generated by the image processing described above (hereinafter, simply referred to as image signal also). The image processing unit 41 may perform gain adjustment according to the brightness of an image. The image processing unit 41 is constituted of a general-purpose processor, such as a central processing unit (CPU), or a dedicated purpose processor including various kinds of arithmetic circuits that perform specific functions, such as an application specific integrated circuit (ASIC).

Moreover, the image processing unit 41 may have a configuration including a frame memory that holds the R image data, the G image data, and the B image data.

The synchronization-signal generating unit 42 generates a clock signal (synchronization signal) to be a reference for operations of the processing device 4, and outputs the generated synchronization signal to the light source device 3, the image processing unit 41, the control unit 44, and the endoscope 2. The synchronization signal generated by the synchronization-signal generating unit 42 includes a horizontal synchronization signal and a vertical synchronization signal.

Therefore, the light source device 3, the image processing unit 41, the control unit 44, and the endoscope 2 operate in synchronization with one another based on the generated synchronization signal.

The input unit 43 is implemented by using a keyboard, a mouse, a switch, and a touch panel, and receives an input of various kinds of signals, such as an operation instruction signal that instructs an operation of the endoscope system 1, and the like. The input unit 43 may include a switch provided in the operating unit 22, or a portable terminal, such as an external tablet type computer.

The control unit 44 performs drive control of the respective components including the imaging device 244 and the light source device 3, and input/output control of information with respect to the respective components. The control unit 44 refers to control information data (for example, read out timing) for imaging control stored in the storage unit 45, and transmits it as a drive signal to the imaging device 244 through a predetermined signal wire included in the bundled cable 245. The control unit 44 is constituted of a general purpose processor, such as a CPU, or a dedicated purpose processor including various kinds of arithmetic circuits that perform specific functions, such as an ASIC.

The storage unit 45 stores various kinds of programs to operate the endoscope system 1, and data including various kinds of parameters necessary for the operation of the endoscope system 1. Moreover, the storage unit 45 stores identification information of the processing device 4. The identification information includes inherent information (ID) of the processing device 4, a model year, specification information, and the like. Moreover, the storage unit 45 includes an illumination-information storage unit 451 that stores information about arrangement of the light sources included in the light source device 3, and the like. The illumination-information storage unit 451 stores, for example, light emitting order of the light sources according to a set light amount (a light amount of illumination light emitted by the light source device 3 in this case).

Furthermore, the storage unit 45 stores various kinds of programs including an image-acquisition processing program to perform an image-acquisition processing method of the processing device 4. The various kinds of programs can be stored in a computer-readable recording medium, such as a hard disk, a flash memory, a compact disk read-only memory (CD-ROM), a digital versatile disk read-only memory (DVD-ROM), and a flexible disk, to be widely distributed. Note that the various kinds of programs described above can also be acquired by downloading through a communication network. The communication network herein is implemented by, for example, an existing public line network, a local area network (LAN), a wide area network (WAN), or the like, and may be of either wired or wireless communication.

The storage unit 45 having the configuration as described above is implemented by using a ROM in which the various kinds of programs are installed in advance, a random access memory (RAM), a hard disk, or the like that stores arithmetic parameters and data of respective processing.

The display device 5 displays a display image corresponding to an image signal received from the processing device 4 (image processing unit 41) through a video cable. The display device 5 is constituted of a monitor of a liquid crystal, an organic electro luminescence (EL), or the like.

Figure 3:
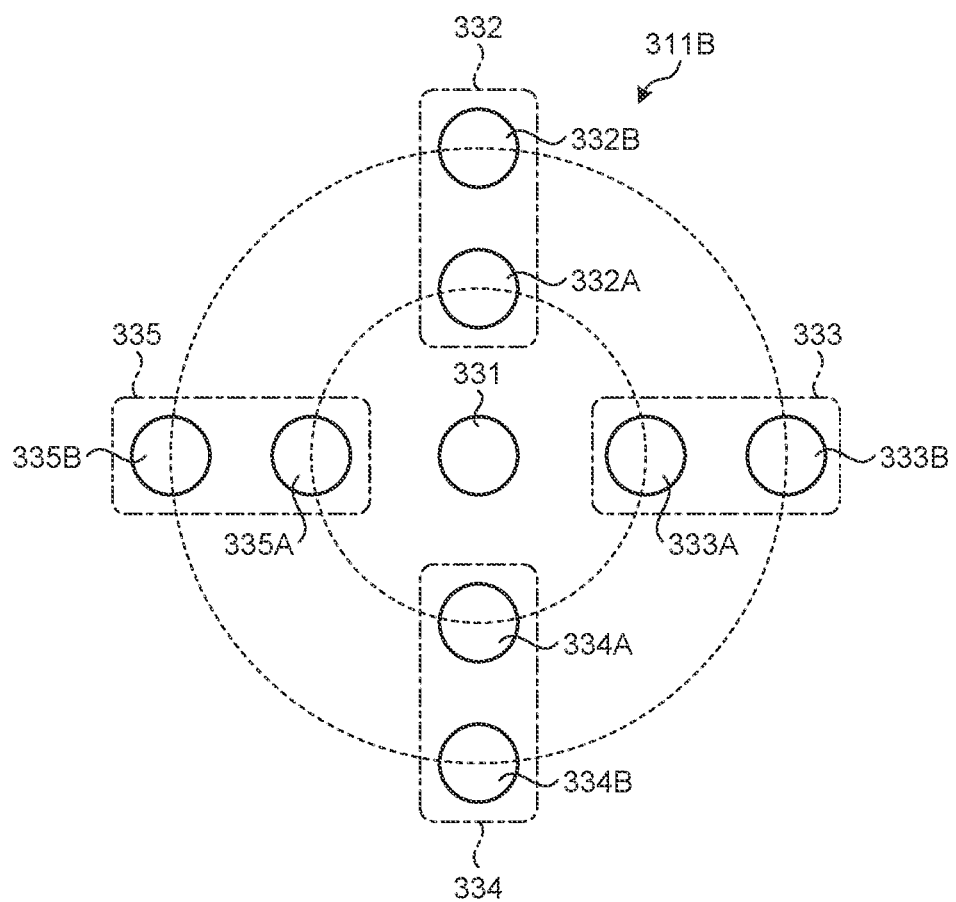
FIG. 3 is a diagram for explaining an arrangement of light sources of a light source device included in the endoscope system according to the first embodiment.
Figure 4A:
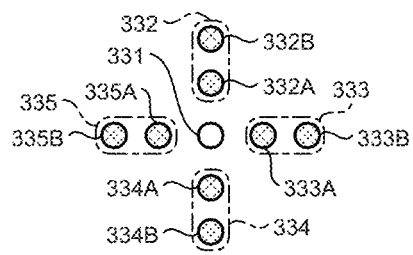
FIGS. 4A-4E are diagrams for explaining light-on order of the light sources of the light source device included in the endoscope system according to the first embodiment.
Figure 4B:
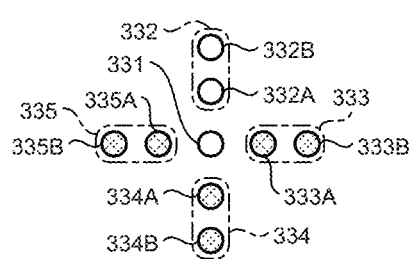
Figure 4C:
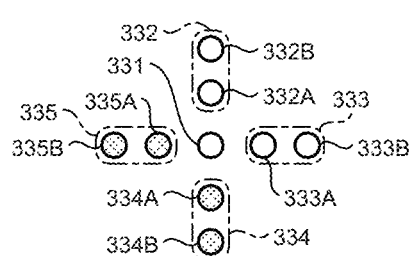
Figure 4D:
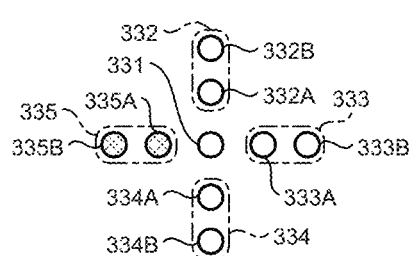
Figure 4E:
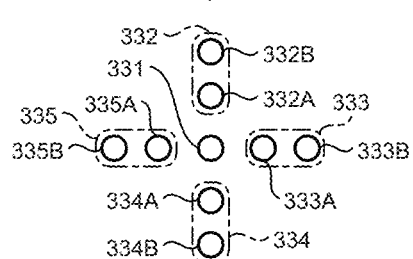

Subsequently, a configuration of the light source included in the light source device 3 will be explained, referring to FIG. 3. FIG. 3 is a diagram for explaining an arrangement of the light sources of the light source device included in the endoscope system according to the first embodiment. In each of the light source groups, plural light sources are provided in the same arrangement. Hereinafter, the arrangement of the light sources of the first light-source group 311B will be explained, referring to FIG. 3. In the second light-source group 311G and the third light-source group 311R also, the light sources are arranged in the similar manner.

The first light-source group 311B includes a first light source 331 (first light emitter) constituted of a single light source, and a second light source 332 to a fifth light source 335 that are constituted of two light sources as one set. The second light source 332 to the fifth light source 335 are arranged coaxially about the first light source 331. The second light source 332 to the fifth light source 335 respectively correspond to partial light emitters, and constitutes a second light emitter as a whole. Light emitted from the first light source 331 corresponds to first light. Moreover, light emitted from the second light source 332 to the fifth light source 335 corresponds to second light. The second light is constituted of light emitted from at least one light source out of the second light source 332 to the fifth light source 335, and it can be light emitted from a single light source (for example, the second light source 332 only), and can be combined light of light respectively emitted from multiple light sources (for example, all of the second light source 332 to the fifth light source 335).

The first light source 331 is constituted of a semiconductor laser. The first light source 331 has a maximum light emitting amount smaller than a maximum light emitting amount of the second light source 332 to the fifth light source 335, and functions as a light source of fine adjustment.

The second light source 332 includes two light sources (light sources 332A, 332B) constituted of a semiconductor laser. The light sources 332A, 332B are respectively arranged on a straight line passing through the first light source 331. This straight line is a straight line that extends in a direction of diameter of a circle having the first light source 331 in the center. In FIG. 3, the light sources 332A, 332B are arranged sequentially in order of the light sources 332A, 332B from the first light source 331 side.

The third light source 333 includes two light sources (light sources 333A, 333B) that are constituted of a semiconductor laser. The light sources 333A, 333B are respectively arranged on a straight line passing through the first light source 331. This straight line is a straight line that extends in a direction of diameter of a circle having the first light source 331 in the center, and is a straight line perpendicular to the straight line on which the second light source 332 is arranged. In FIG. 3, the light sources 333A, 333B are arranged sequentially in order of the light sources 333A, 333B from the first light source 331 side.

The fourth light source 334 includes two light sources (light sources 334A, 334B) that are constituted of a semiconductor laser. The light sources 334A, 334B are respectively arranged on a straight line passing through the first light source 331. This straight line is a straight line that extends in a direction of diameter of a circle having the first light source 331 in the center, and is a straight line passing through the second light source 332. In other words, the fourth light source 334 is arranged on the opposite side to the second light source 332 relative to the first light source 331. In FIG. 3, the light sources 334A, 334B are arranged sequentially in order of the light sources 333A, 333B from the first light source 331 side.

The fifth light source 335 includes two light sources (light sources 335A, 335B) that are constituted of a semiconductor laser. The light sources 335A, 335B are respectively arranged on a straight line passing through the first light source 331. This straight line is a straight line that extends in a direction of diameter of a circle having the first light source 331 in the center, and is a straight line passing through the third light source 333. In other words, the fifth light source 335 is arranged on the opposite side to the third light source 333 relative to the first light source 331. In FIG. 3, the light sources 335A, 335B are arranged sequentially in order of the light sources 335A, 335B from the first light source 331 side.

In the first light source group 311B, the light sources 332A, 333A, 334A, 335A are arranged coaxially, and the light sources 332B, 333B, 334B, 335B are arranged coaxially.

Moreover, in the first light source group 311B, the light modulation resolution of the first light source 331 is higher than the light modulation resolution of the second light source 332 to the fifth light source 335. Conversely, because the second light source 332 to the fifth light source 335 have the configuration in which two light sources are lit simultaneously, the light modulation resolution of the second light source 332 to the fifth light source 335 is lower than the light modulation resolution of the first light source 331. The light modulation resolution signifies the brightness when intervals of light modulation value in a control circuit is the same, and the resolution is higher when the brightness is lower. The first light source 331 has smaller adjustment width is smaller than that of the second light source 332 to the fifth light source 335, and fine adjustment is possible.

The illumination control unit 32 turns on and off the respective light sources in order set in advance. In the first embodiment, the illumination control unit 32 turns on the first light source 331, the second light source 332, the third light source 333, the fourth light source 334, and the fifth light source 335 sequentially in this order, and turns off the fifth light source 335, the fourth light source 334, the third light source 333, the second light source 332, and the first light source 331 sequentially in this order. The illumination control unit 32 turns off the light sources in inverse order to the light-on order. Note that there is a case in which a light source in a later stage is not turned on depending on a set light amount.

FIGS. 4A-4E are diagrams for explaining the light-on order of the light sources of the light source device included in the endoscope system according to the first embodiment. FIGS. 4A-4E illustrate a case in which all of the light sources are turned on. In FIGS. 4A-4E, an uncolored (not hatched) circle (light source) indicates a light-on state, and a hatched circle indicates a light-off state. Under control of the illumination control unit 32, first, the first light source 331 is turned on (refer to FIG. 4A). Subsequently, the second light source 332 is turned on (refer to FIG. 4). Next, the third light source 333 is turned on (refer to FIG. 4C), and then the fourth light source 334 is turned on (refer to FIG. 4D). Finally, the fifth light source 335 is turned on (refer to FIG. 4E). Subsequently, the second light source 332 is turned on (refer to (b) in FIG. 4). Next, the third light source 333 is turned on (refer to (c) in FIG. 4), and then the fourth light source 334 is turned on (refer to (d) in FIG. 4). Finally, the fifth light source 335 is turned on (refer to (e) in FIG. 4).

FIGS. 5A-5F are diagrams for explaining light-off order of the light sources of the light source device included in the endoscope system according to the first embodiment. FIGS. 5A-5F illustrate the light-off order when all of the light sources are turned on in the order illustrated in FIGS. 4A-4E. In FIGS. 5A-5F, similarly to FIGS. 4A-4E, an uncolored circle indicates a light-on state, and a hatched circle indicates a light-off state. Under control of the illumination control unit 32, first, the fifth light source 335 is turned off (refer to FIG. 5B) from the state in which all of the light sources are turned on (refer to FIG. 5A). Subsequently, the fourth light source 334 is turned off (refer to FIG. 5C). Next, the third light source 333 is turned off (refer to FIG. 5D), and thereafter, the second light source 332 is turned off (refer to FIG. 5E). Finally, the first light source 331 is turned off (refer to FIG. 5F).

In the first embodiment explained above, in a configuration in which eight light sources coaxially arranged, and one light source arranged in the center thereof are provided, and illumination light of one color component is emitted, the eight light sources are divided into four groups, and lighting is controlled according to a set light amount. According to the first embodiment, because the light source to be turned on is fixed to the first light source 331, it is possible to control a light amount of the illumination light while suppressing variations of light properties of the illumination light in a dark scene. Moreover, according to the first embodiment, the respective light sources in the second light source 332 to the fifth light source 335 are controlled collectively, control units can be reduced, and consequently, an increase in size of a circuit scale for light sources can be suppressed in a configuration including plural light sources.

Figure 6:
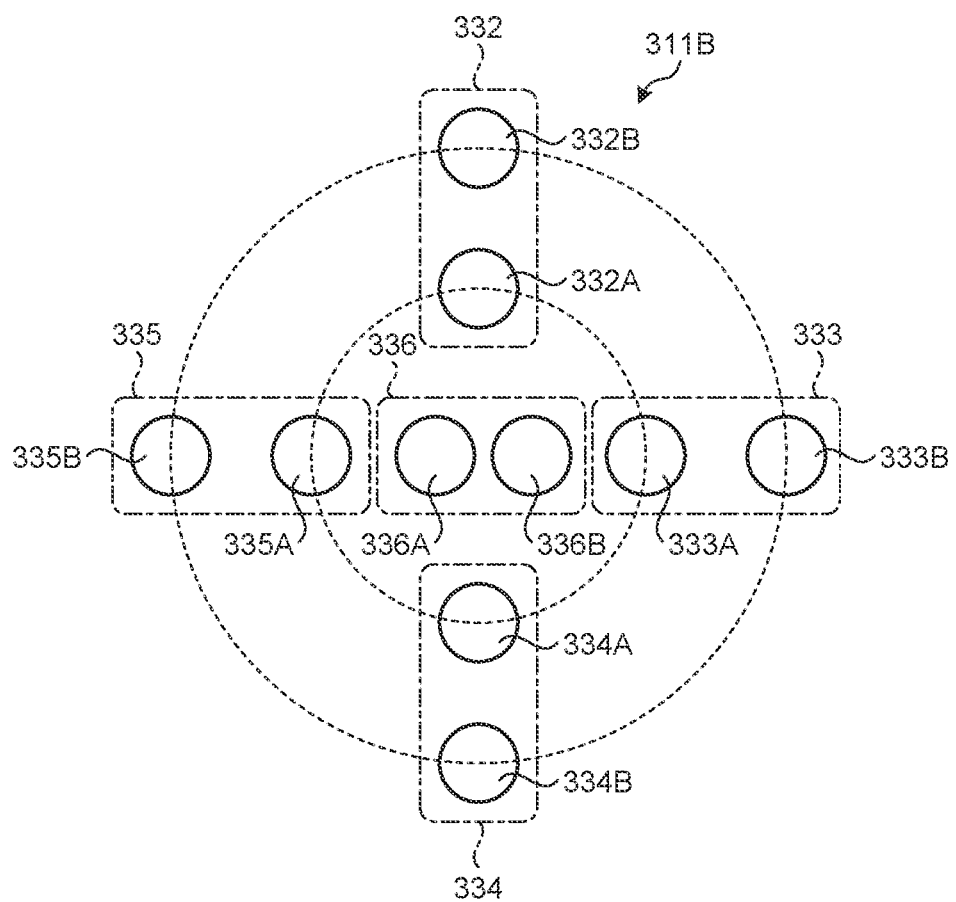
FIG. 6 is a diagram for explaining an arrangement of light sources of a light source device included in an endoscope system according to a second embodiment.
Figure 8A:
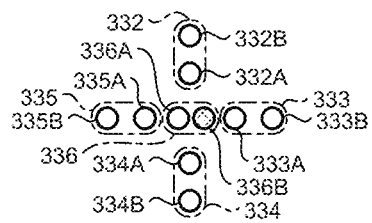
FIGS. 8A-8F are diagrams for explaining light-off order of the light sources in the first light-on mode of the light source device included in the endoscope system according to the second embodiment.
Figure 8B:
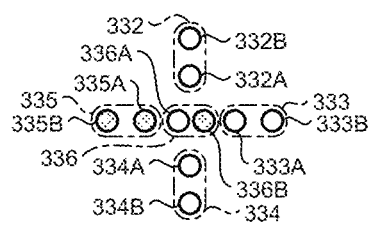
Figure 8C:
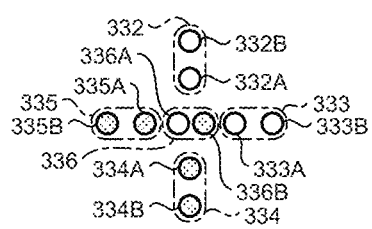
Figure 8D:
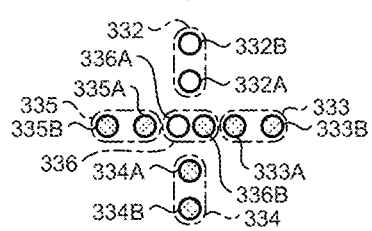
Figure 8E:
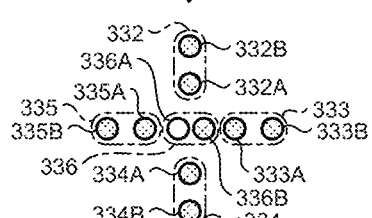
Figure 8F:
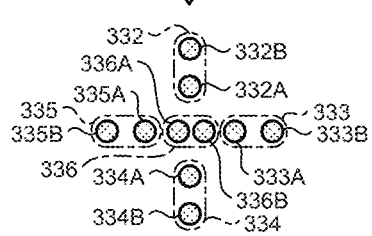

Next, a second embodiment of the present disclosure will be explained, referring to FIG. 6. An endoscope system according to the second embodiment has the same configuration as that of the first embodiment, except that an arrangement of the light sources in the light source device 1 of the endoscope system 1 described above is changed. Hereinafter, the arrangement of the light sources different from the configuration of the first embodiment, and the illumination control therewith will be explained. FIG. 6 is a diagram for explaining an arrangement of light sources of a light source device included in the endoscope system according to the second embodiment. Hereinafter, an arrangement of the light sources in the first light source group 311B will be explained, referring to FIG. 6. Similarly to the first embodiment, in the second light source group 311G and the third light source group 311R also, the light sources are arranged in the similar manner.

The first light source group 311B according to the second embodiment includes a first light source 336 (the first light emitter) constituted of two light sources as a set, and the second light sources 332 to the fifth light sources 335 that are constituted of two light sources as a set. The second light source 332 to the fifth light source 335 are coaxially arranged having the first light source 336 in the center. Hereinafter, the first light source 336 having the configuration different from the first embodiment will be explained.

The first light source 336 has two light sources (light sources 336A, 336B) constituted of a semiconductor laser. In the first light source 336, only one light source out of the light sources 336A, 336B is turned on. In the first light source 336, the first light is emitted from the light source 336A or the light source 336B. Therefore, the first light source 336 has a maximum light emitting amount smaller than a maximum light emitting amount of the second light source 332 to the fifth light source 335, and functions as a light source of fine adjustment.

The light sources 336A, 336B are respectively arranged on a straight line that passes through the center of a circuit on which the second light source 332 to the fifth light source 335 are arranged, and on which the third light source 333 and the fifth light source 335 are arranged. The light sources 336A, 336B may be arranged on a straight line on which the second light source 332 and the fourth light source 334 are arranged, or may be arranged on a straight line that is different from the straight line on which the second light source 332 to the fifth light source 335 are arranged.

In the first light source group 311B, because only one out of the two light sources (the light sources 336A, 336B) is turned on, the light modulation resolution of the first light source 336 is higher than the light modulation resolution of the second light source 332 to the fifth light source 335.

The illumination control unit 32 turns on and off the respective light sources in order set in advance. Specifically, the illumination control unit 32 turns on and off the light sources according to either mode out of two light-on modes. For example, in a first light-on mode, the light source 336A, the second light source 332, the third light source 333, the fourth light source 334, the fifth light source 335 are sequentially turned on in this order, and the fifth light source 335, the fourth light source 334, the third light source 333, the second light source 332, and the light source 336A are sequentially turned off in this order.

FIGS. 7A-7E are diagrams for explaining light-on order of the light sources in the first light-on mode of the light source device included in the endoscope system according to the second embodiment. FIGS. 7A-7E illustrate a case in which all of the light sources are turned on. Hereinafter, an uncolored circle indicates a light-on state, and a hatched circle indicates a light-off state. Under control of the illumination control unit 32, first, the light source 336A of the first light source 336 is turned on (refer to FIG. 7A). Subsequently, the second light source 332 is turned on (refer to FIG. 7B). Next, the third light source 333 is turned on (refer to FIG. 7C), and thereafter, the fourth light source 334 is turned on (refer to FIG. 7D). Finally, the fifth light source 335 is turned on (refer to FIG. 7E). In the first light-on mode, the light source 336B of the first light source 336 is not turned on.

FIGS. 8A-8F are diagrams for explaining light-off order of the light sources in the first light-on mode of the light source device included in the endoscope system according to the second embodiment. FIGS. 8A-8F illustrate the light-off order when all of the light sources are turned on in the order illustrated in FIGS. 7A-7E. Under control of the illumination control unit 32, first, the fifth light source 335 is turned off (refer to FIG. 8B) from the state in which all of the light sources are turned on (refer to FIG. 8A) in the light-on order illustrated in FIGS. 7A-7E. Subsequently, the fourth light source 334 is turned off (refer to FIG. 8C). Next, the third light source 333 is turned off (refer to FIG. 8D), and thereafter, the second light source 332 is turned off (refer to FIG. 8E). Finally, the light source 336A is turned off (refer to FIG. 8F).

On the other hand, in the second light-on mode, the light source 336B, the fifth light source 335, the fourth light source 334, the third light source 333, and the second light source 332 are sequentially turned on in this order, and the second light source 332, the third light source 333, the fourth light source 334, the fifth light source 335, and the light source 336B are sequentially turned off in this order. Note that there is a case in which a light source in a later stage is not turned on depending on a set light amount.

FIGS. 9A-9E are diagrams for explaining light-on order of the light sources in a second light-on mode of the light source device included in the endoscope system according to the second embodiment. FIGS. 9A-9E illustrate a case in which all of the light sources are turned on. Under control of the illumination control unit 32, first, the light source 336B of the first light source 336 is turned on (refer to FIG. 9A). Subsequently, the fifth light source 335 is turned on (refer to FIG. 9B). Next, the fourth light source 334 is turned on (refer to FIG. 9C), and thereafter, the third light source 333 is turned on (refer to FIG. 9D). Finally, the second light source 332 is turned on (refer to FIG. 9E). In the second light-on mode, the light source 336A of the first light source 336 is not turned on.

FIGS. 10A-10F are diagrams for explaining light-off order of the light sources in the second light-on mode of the light source device included in the endoscope system according to the second embodiment. FIGS. 10A-10F illustrate the light-off order when all of the light sources are turned on in the light-on order illustrated in FIGS. 9A-9E. Under control of the illumination control unit 32, the second light source 332 is turned off (refer to FIG. 10B) from the state in which all of the light sources are turned on (refer to FIG. 10A) in the light-on order illustrated in FIGS. 9A-9E. Subsequently, the third light source 333 is turned off (refer to FIG. 10C). Next, the fourth light source 334 is turned off (refer to FIG. 10D), and thereafter, the fifth light source 335 is turned off (refer to FIG. 10E). Finally, the light source 336B is turned off (refer to FIG. 10F).

When the light sources are continuously lit in the first light-on mode, the utilization rate of the second light source 332 to the fifth light source 335 decreases in order of the second light source 332, the third light source 333, the fourth light source 334, and the fifth light source 335. For example, setting the utilization rate of the first light source 336 (the light source 336A or the light source 336B) to 100%, it is assumed that the utilization rate of the second light source 332 is 80%, the utilization rate of the third light source 333 is 60%, the utilization rate of the fourth light source is 40%, and the utilization rate of the fifth light source 335 is 20% when the first light source 336 to the fifth light source 335 are turned on and off in uniform timing. In this case, grouping the second light source 332 of the highest utilization rate and the fifth light source 335 of the lowest utilization rate into a set, and grouping the third light source 333 and the fourth light source 334 of the intermediate utilization rate into a set, in the second light-on mode, the light-on order is switched from the first light-on mode in each set. By appropriately switching the second light-on mode with switched light-on order and the first light-on mode, the utilization rate of the light sources in each set can be equalized. Consequently, the utilization rate (light-on time) of the second light source 332 to the fifth light source 335 can be equalized.

The first and the second light-on modes can be switched under control of the control unit 44, and time required for the illumination control, either one of the number of days of operation, and the life of the light source 336A (or the light source 336B) can be the trigger. Conditions to perform the switching control are stored in the illumination-information storage unit 451 in advance.

In the second embodiment explained above, in a configuration in which eight light sources coaxially arranged, and one light source arranged in the center thereof are provided similarly to the first embodiment, and illumination light of one color component is emitted, the eight light sources are divided into four groups, and lighting is controlled according to a set light amount. According to the second embodiment, because the light source to be turned on first is fixed to the first light source 336, it is possible to control a light amount of the illumination light while suppressing variations of light properties of the illumination light in a dark scene. Moreover, according to the second embodiment, the respective light sources in the second light source 332 to the fifth light source 335 are controlled collectively, control units can be reduced, and consequently, an increase in size of a circuit scale can be suppressed.

Moreover, in the second embodiment, two pieces of the light sources are provided in the first light source 336, and the light source to be turned on is switched in predetermined timing, and the light-on order of the light sources grouped into a set according to the maximum utilization rate (in this example, the second light source 332 and the fifth light source 335, the third light source 333 and the fourth light source 334) is switched. By the switching of the light-on mode described above, the life of the light sources as a whole in the light source device can be increased.

Furthermore, in the second embodiment, because it is configured to control the light-on order, grouping the light sources of the highest and the lowest utilization rates into a set, the light-on control of the light sources in which a difference in the utilization rate among the light sources is minimized is performed, and the life of the light sources can be increased.

The grouping of the light sources may be determined by using a randomly extracted function (random number) each time of operation. Also when the grouping is determined randomly, the utilization rates are equalized as the number of operation increases.

In the second embodiment described above, it has been explained that light is emitted only from one of the light sources (the light source 336A or the light source 336B) of the first light source 336 in the first light source group 311B, but light may be emitted from both the light source 336A and the light source 336B. In this case, for example, light emitted from each light source is ½ each of an amount of light emitted as the first light source 336.

Furthermore, in the second embodiment described above, the life of the light sources are increased by grouping the light sources according to the utilization rate in the first light-on mode and switching the light-on order, but the precedence of the light sources to be turned on may be rotated. For example, a light-on order in which the second light source 332 is given first priority to be turned on, a light-on order in which the third light source 333 is given first priority to be turned on, a light-on order in which the fourth light source 334 is given first priority to be turned on, and a light-on order in which the fifth light source 335 is given first priority to be turned on are rotated. Switching of the light sources to be prioritized is performed on the conditions explained in the second embodiment described above.

Moreover, in the second embodiment described above, light (the first light) may be emitted from both of the light sources 336A and 336B simultaneously. In this case, the first light source 336 and the second light source 332 to the fifth light source 335 have the same light modulation resolution. Also in this case, because the light source to be turned on first is fixed to the first light source 336, and the 10 pieces of the light sources are controlled in a set of two pieces, control units can be reduced, while suppressing variations of light properties of the illumination light in a dark scene. Furthermore, if light of a desired light amount can be emitted, the number of light sources in each of the first light source 336 and the second light source 332 to the fifth light source 335 can be one.

Moreover, although it has been explained in the first and the second embodiments described above that the first light source group 311B has the first light source 331 (or 336) and four pieces of light sources (the second light source 332 to the fifth light source 335) arranged therearound, for example, as long as having the maximum light emitting amount larger than that of the first light source, and having the light modulation resolution lower than that of the first light source, the light source (the first light emitter) to be provided around the first light source (the second light emitter) may be one piece. Moreover, although it has been explained that the second light source 332 to the fifth light source 335 have two pieces of light sources, they may be configured to have one piece of light source, or three or more pieces of light sources. Furthermore, as long as light can be supplied to the light guide, the arrangement of the first light source to the fifth light source is not limited to the arrangement illustrated in FIGS. 3 and 4 described above.

Moreover, although it has been explained in the first and the second embodiment described above that the light source device 3 is configured to be a separate unit from the endoscope 2, for example, a configuration in which the light source device is arranged in the endoscope 2, such that the semiconductor laser is arranged at a distal end of the endoscope 2, may be applied also. Furthermore, the function of the processing device 4 may be added to the endoscope 2.

Moreover, although it has been explained in the first and the second embodiments described above that the light source device 3 is a separate unit from the processing devices 4, 3A, the light source device 3 and the processing device 4 may be unified in one unit, and for example, the light source unit 31 and the illumination control unit 32 may be provided in the processing device 4.

Furthermore, in the first and the second embodiments, the light source device 3 may be constituted of an LED light source instead of the semiconductor laser, or may be configured to include a white light source (for example, a xenon lamp or a halogen lamp) and a revolving filter having three transmission filters that pass a wavelength band of red, a wavelength band of green, and a wavelength band of blue, respectively on an optical path of illumination light to be emitted by the white light source, and to irradiate illumination light including respective wavelength bands of red, green, and blue by revolving the revolving filter.

Moreover, although it has been explained in the first and the second embodiments described above that the endoscope system according to the present disclosure is the endoscope system 1 using the flexible endoscope 2, a subject of observation of which is a living tissue inside a body of a subject and the like, it can be applied also to a rigid endoscope, an endoscope system for an industrial use to observe properties of a material, a capsule endoscope, a fiberscope, and an endoscope system in which a camera head is attached to an eyepiece of an optical endoscope, such as an optical borescope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device for use with an endoscope, the light source device comprising:
   a first light emitter configured to emit first light;
   a second light emitter configured to emit second light;
   a third light emitter configured to emit third light;
   a fourth light emitter configured to emit fourth light; and
   an illumination controller configured to control the first light emitter, the second light emitter, the third light emitter and the fourth light emitter such that:
      in a first state, each of the first light emitter emits the first light, the second light emitter is off, the third light emitter is off and the fourth light emitter is off;
      in a second state, different from the first state, each of the first light emitter emits the first light, the second light emitter emits the second light, the third light emitter is off, and the fourth light emitter is off; and
      in a third state different from each of the first state and the second state, each of the first light emitter emits the first light, the second light emitter emits the second light, the third light emitter emits the third light, and the fourth light emitter is off;
   wherein the second light emitter, the third light emitter and the fourth light emitter are provided at a same diameter having a first center of the first light emitter.

2. The light source device according to claim 1, wherein the first light emitter has a first light modulation resolution, and
   the second light emitter has a second light modulation resolution lower than the first light modulation resolution.

3. The light source device according to claim 1, wherein the first light emitter is configured to emit the first light at a first light amount,
   the second light emitter is configured to emit the second light at a second light amount, and
   the illumination controller is further configured to one of:
      switch from the first state to the second state; or
      cause the first light emitter to turn off according to a set light amount.

4. The light source device according to claim 3, wherein the third light emitter is configured to emit the third light at a third light amount,
   the first light amount is determined to be smaller than the set light amount; and
   the illumination controller is further configured to one of:
      switch from the second state to the third state; or
      switch from the second state to the first state according to the set light amount.

5. The light source device according to claim 4, wherein the fourth light emitter is configured to emit the fourth light at a fourth light amount, the illumination controller is further configured to:
control the first light emitter, the second light emitter, the third light emitter and the fourth light emitter such that in a fourth state, each of the first light emitter emits the first light, the second light emitter emits the second light, the third light emitter emits the third light, and the fourth light emitter emits the fourth light; and
one of switch from the third state to the fourth state; or switch from the third state to the second state according to the set light amount.

6. The light source device according to claim 5, further comprising:
a fifth light emitter configured to emit a fifth light at a fifth light amount,
the illumination controller is further configured to:
control the first light emitter, the second light emitter, the third light emitter, the fourth light emitter and the fifth light emitter such that in a fifth state, each of the first light emitter emits the first light, the second light emitter emits the second light, the third light emitter emits the third light, the fourth light emitter emits the fourth light, and the fifth light emitter emits the fifth light; and
one of switch from the fourth state to the fifth state; switch from the fourth state to the third state according to the set light amount.

7. The light source device according to claim 1, wherein the first light emitter includes one or more semiconductor lasers configured to emit the first light.

8. The light source device according to claim 1, wherein the illumination controller is further configured to control the first light emitter, the second light emitter, the third light emitter and the fourth light emitter such that in a fourth state, each of the first light emitter emits the first light, the second light emitter is off, the third light emitter is off, and the fourth light emitter emits the fourth light.

9. The light source device according to claim 1, wherein the illumination controller is configured to switch, in order, from the first state, to the second state and to the third state, and
after the switching, switch, in order, from the third state, to the second state and to the first state.

10. The light source device according to claim 1, wherein the first light emitter includes a first light source and a second light source, and
in the first state, only one of the first light source or the second light source is turned on according to a first utilization rate of the first light source and a second utilization rate of the second light source.

11. The light source device according to claim 1, wherein the second light emitter includes a first light source and a second light source provided in a first radial direction from the first light emitter,
the third light emitter includes a third light source and a fourth light source provided in a second radial direction from the first light emitter,
the first light source and the third light source are provided at a first diameter from the first light emitter,
the second light source and the fourth light source are provided at a second diameter from the first light emitter, and
the first diameter is smaller than the second diameter.

12. The light source device according to claim 11, wherein the first light source has a first center,
the second light source has a second center,
the third light source has a third center,
the fourth light source has a fourth center,
the first center and the second center are on a first radial line extending from a center of the first light emitter, and
the third center and the fourth center are on a second radial line extending from the center of the first light emitter.

13. The light source device according to claim 1, further comprising:
a fifth light emitter configured to emit a fifth light at a fifth light amount, and
wherein the first light emitter is between the second light emitter and the fourth light emitter, and
the first light emitter is between the third light emitter and the fifth light emitter.

14. The light source device according to claim 1, wherein the second light emitter has a second center,
the third light emitter has a third center,
the fourth light emitter has a fourth center, and
the second center, the third center and the fourth center are at the same diameter from the first light emitter.

15. An endoscope system comprising:
an endoscope; and
the light source device according to claim 1.

16. A control method of a light source for use with an endoscope, the light source including a first light emitter configured to emit first light; a second light emitter configured to emit second light, a third light emitter configured to emit third light and a fourth light emitter configured to emit fourth light, the method comprising:
controlling the first light emitter, the second light emitter, the third light emitter and the fourth light emitter such that:
in a first state, each of the first light emitter emits the first light, the second light emitter is off, the third light emitter is off and the fourth light emitter is off;
in a second state, different from the first state, each of the first light emitter emits the first light, the second light emitter emits the second light, the third light emitter is off, and the fourth light emitter is off; and
in a third state different from each of the first state and the second state, each of the first light emitter emits the first light, the second light emitter emits the second light, the third light emitter emits the third light, and the fourth light emitter is off;
wherein the second light emitter, the third light emitter and the fourth light emitter are provided at a same diameter having a first center of the first light emitter.

17. The control method of the light source according to claim 16, further comprising:
switching, in order, from the first state, to the second state and to the third state; and
after the switching, switching, in order, from the third state, to the second state and to first state.

18. The control method of the light source according to claim 16, wherein the first light emitter is configured to emit the first light at a first light amount and the second light emitter is configured to emit the second light at a second light amount, and
the method further comprising one of:
switching from the first state to the second state; or causing the first light emitter to turn off according to a set light amount.

19. A light source device for use with an endoscope, the light source device comprising:
a first light emitter configured to emit first light;
a second light emitter configured to emit second light;

a third light emitter configured to emit third light;
a fourth light emitter configured to emit fourth light; and
an illumination controller configured to control the first light emitter, the second light emitter and the third light emitter such that:
   in a first state, each of the first light emitter emits the first light, the second light emitter is off, and the third light emitter is off and the fourth light emitter is off; and
   in a second state, each of the first light emitter emits the first light, the second light emitter emits the second light, and the third light emitter is off, and the fourth light emitter is off;
   in a third state different from each of the first state and the second state, each of the first light emitter emits the first light, the second light emitter emits the second light, the third light emitter emits the third light, and the fourth light emitter is off,
wherein the first light emitter includes a first light source and a second light source,
in the first state, only one of the first light source or the second light source is turned on according to a first utilization rate of the first light source and a second utilization rate of the second light source.

\* \* \* \* \*